United States Patent [19]

Newallis et al.

[11] 3,972,928
[45] Aug. 3, 1976

[54] REGULATING PLANT GROWTH WITH QUATERNARY PHOSPHONIUM ALIPHATIC CARBOXAMIDE SALTS

[75] Inventors: Peter E. Newallis, Leawood, Kans.; Albert J. Poje, Grandview, Mo.

[73] Assignee: Baychem Corporation, New York, N.Y.

[22] Filed: Nov. 15, 1971

[21] Appl. No.: 198,950

[52] U.S. Cl. ............................ 260/561 P; 71/86; 260/247.2 A; 260/293.86; 260/347.3; 260/239 B; 260/503; 260/513.7; 260/520 C; 260/521 R; 260/535 H; 260/535 R; 260/539 A; 260/540; 260/562 N; 260/562 R; 260/569; 260/607 R; 424/211; 428/276
[51] Int. Cl. ........................................ C07c 103/30
[58] Field of Search ......... 260/561 P, 562 R, 562 N

[56] References Cited
UNITED STATES PATENTS

| | | | |
|---|---|---|---|
| 3,187,043 | 6/1965 | Speziale et al. | 260/561 P X |
| 3,573,299 | 3/1971 | Andrews et al. | 260/247.7 |
| 3,689,601 | 9/1972 | Grayson et al. | 260/561 P X |

OTHER PUBLICATIONS

Fuerst et al., Chem. Abstracts, vol. 59, 3948f.
Fishwick, Chem. Abstracts, vol. 60, 4281a.
CIBA Ltd., Chem. Abstracts, vol. 72, 55650d.
Quinkert et al., Chem. Abstracts, vol. 75, 88272x.

Primary Examiner—Lewis Gotts
Assistant Examiner—Ethel G. Love
Attorney, Agent, or Firm—Burgess, Dinklage & Sprung

[57] ABSTRACT

Regulating plant growth with carbamoyl and substituted carbamoyl alkyl trihydrocarbyl phosphonium organic and inorganic salts of the formula

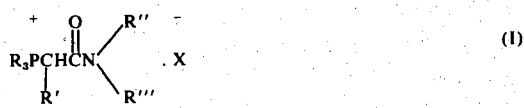

in which
R is alkyl of 1–14 carbons, phenyl, tolyl or dimethylamino;
R' is hydrogen or lower alkyl;
R" and R'" each is hydrogen, alkyl of 1–14 carbon atoms, cycloalkyl of 3–7 carbon atoms, alkenyl of 2–6 carbon atoms, cyanoalkyl having 1–4 carbon atoms in each corresponding alkyl moiety, aralkyl having 1–4 carbon atoms in each corresponding alkyl moiety and optionally substituted with 1–3 chlorine atoms, furfuryl, phenyl, phenyl substituted with 1–3 chloro or methoxy or methylthio or 1–2 alkyl groups having 1–3 carbon atoms; or
R" and R'" combined are piperidino, morpholine, 3-aza (3,2,2) bicycloheptyl; and
X⁻ is monovalent anion.
Many of the cmpounds are new.

9 Claims, No Drawings

REGULATING PLANT GROWTH WITH QUATERNARY PHOSPHONIUM ALIPHATIC CARBOXAMIDE SALTS

The present invention relates to and has for its objects the regulation of plant growth and compositions therefor containing phosphonium salts, i.e. (tri- alkyl, phenyl, substituted phenyl, alkylamino) carbamoyl alkyl and N and N, N- (mono- and di-) carbamoyl alkyl substituted with alkyl, cycloalkyl, alkenyl, alkoxyalkyl, cyanoalkyl, aralkyl, furfuryl, substituted aryl (mono-, di- and trichloro, methoxy, alkyl, methylthio, trifluoromethyl), phenyl and heterocyclics such as piperidino and morpholino, the salts represented by inorganic acids, aliphatic and aromatic carboxylic acids, organo-substituted sulfur-containing acids in the form of mixtures with solid and liquid dispersible carrier vehicles, with other and further objects becoming apparent from a study of the within specification and accompanying examples.

It is already known that some phosphonium salts can be used for the control of parasitic worms such as nematodes French Pat. No. 1,535,554), and others for the protection of wool from moths (J. Prakt, Chem. 4 288 (1962), *J. Soc. Org. Syn.* Chem. (Japan) 8, 211 (1950). However, it is not believed that such phosphonium salts are known to possess plant-growth-regulating properties.

It has now been found, in accordance with the present invention, that the particular phosphonium salts of this invention, some of which are known as nematocides and wool protection agents, are also usable according to the present invention and have a high degree of growth-regulating activity. Some of these compounds may be used in a new way for stunting the growth of monocotyledonous and dicotyledonous crop and weed plants, ornamentals, shrubs and trees. Selected compounds for this invention may be beneficial to crops such as soybeans and snapbeans by increasing the yield and/or protein content of such plants. Some of the compounds of this invention could cause the formation of abscission layers of fruit or buds, so that the number of buds or fruit dropping from a plant and/or the ease of dropping of such fruit may be regulated. Other types of beneficial effects on certain plants may be anticipated from the above described biological effects. These include the regulation of the setting fruit of spermatophytic plants, increasing the resistance of plants to frost or drought damage, increasing the yield of sugarbeets or cane and their sugar content, causing defoliation of cotton, and increasing the size of flowers and shape of ornamental plants, reduction of the undesirable growth of suckers for plants such as tobacco, inhibition of the sprouting of potatoes, breaking plant dormancy and such similar biological effects.

The plant-growth-regulating compositions and methods of regulating plant growth using such active compounds according to the present invention, therefore, represent a valuable enrichment of the art.

It has been found, in accordance with the present invention, that the particular quaternary phosphonium carboxamide salts of the Formula (I)

in which:
R is alkyl of 1–14 carbons, phenyl, tolyl or dimethylamino;
R' is hydrogen or lower alkyl;
R'' and R''' each is hydrogen, alkyl of 1–14 carbon atoms, cycloalkyl of 3–7 carbon atoms, alkenyl of 2–6 carbon atoms, cyanoalkyl having 1–4 carbon atoms in each corresponding alkyl moiety, aralkyl having 1–4 carbon atoms in each corresponding alkyl moiety and optionally substituted with 1–3 chlorine atoms, furfuryl, phenyl, phenyl substituted with 1–3 chloro or methoxy or methylthio or 1–2 alkyl groups having 1–3 carbon atoms; or
R'' and R''' combined are piperidino morpholino, 3-aza (3,2,2) bicycloheptyl; and
$X^-$ is a monovalent anion,
possess desirable growth-regulating properties.

It has been furthermore found, in accordance with the present invention, that the compounds of Formula (I) above may be produced by a process which comprises reacting the corresponding alpha chloro carboxamide of the formula:

in which:
R', R'', and R''' are the same as defined above, with a tertiary phosphine of the formula

in which:
R is the same as defined above,
optionally in the presence of a solvent.

Surprisingly, many of the phosphonium salts of the present invention are new and exhibit plant-growth-regulating properties. Thus, the instant compounds represent a valuable enrichment of the art.

If, for instance, N, N-diethyl chloroacetamide and tri-n-butyl phosphine are used as starting materials, the course of the reaction can be represented by the following equation:

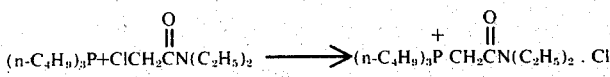

In Formula (I), $X^-$ can represent a wide variety of anions. Some of these can be produced directly from the appropriate starting materials e.g., chlorides, bromides. However, these and many others can be produced by an anion exchange reaction.

The course of the anion exchange reaction in which, for example, diethylaminocarbonylmethyl) tri-n-butyl phosphonium chloride and potassium thiocyanate are used as starting materials can be represented by the following equation:

$$(n\text{-}C_4H_9)_3P^+CH_2\overset{O}{\overset{\|}{C}}N(C_2H_5)_2 \cdot Cl^- + KSCN \longrightarrow (n\text{-}C_4H_9)_3\overset{+}{P}CH_2\overset{O}{\overset{\|}{C}}N(C_2H_5) \cdot SCN^- + KCl$$

Advantageously, in accordance with the present invention, in the various formulae herein, R, each individually, represents straight or branched chain alkyl hydrocarbon of 1–14 carbon atoms such as methyl, ethyl, n- or iso- propyl, n-, iso- or t-butyl, n- or iso amyl, n- or iso hexyl, n- or iso-octyl, nonyl, decyl undecyl, dodecyl, or the like, especially alkyl of up to 8 carbon atoms, particularly lower alkyl and more especially n- or iso propyl, n- or iso butyl; phenyl; lower alkyl-phenyl, such as 2-, 3- or 4-methyl to tert.-butyl-phenyl, or the like, especially $C_{1\text{-}4}$ or $C_{1\text{-}3}$ or $C_{1\text{-}2}$ alkyl-phenyl, and more especially 2-, 3- or 4-methylphenyl, the three R groups being the same or different;

R' represents hydrogen or a lower alkyl hydrocarbon of 1–5 carbon atoms;

R" and R'" each individually represents hydrogen, alkyl hydrocarbon of 1–14 carbon atoms, including straight or branched chains, such as methyl, ethyl, n- or iso-propyl, n-, iso-, sec.- or tert.-butyl, n- or iso-amyl, n- or iso-hexyl, heptyl, octyl, nonyl, decyl, undecyl, dodecyl, tridecyl, tetradecyl, or the like, especially alkyl of 1–8 carbon atoms; alkenyl of 3–6 carbon atoms; cycloalkyl of 3–7 carbon atoms, especially of 6 carbon atoms; cyanolower alkyl having 1–4 carbon atoms in the alkyl moiety; phenyl; phenyl substituted with 1–3 chloro, bromo or lower alkyl radicals of 1–4 carbon atoms such as methyl, ethyl, n- or iso-propyl, n-, iso- or tert-butyl or the like as defined above; lower alkylmercapto having 1–4 carbon atoms in the alkyl moiety; lower alkoxy having 1–4 carbon atoms in the alkyl moiety; fluoro substituted lower alkyl of 1–4 carbon atoms having 1–5 fluoro substituents such as mono- to tri-fluoromethyl, mono- to pentafluoroethyl, n-, and iso-propyl, n-, iso-, sec-, and tert.-butyl, and the like, especially mono- to trifluoro $C_{1\text{-}2}$ alkyl, more especially trifluoro $C_{1\text{-}4}$ or $C_{1\text{-}2}$ alkyl, and most especially trifluoromethyl; benzyl; substituted benzyl which is substituted with 1–3 chlorine atoms or 1–3 lower alkyl radicals of 1–4 carbon atoms; heterocyclicalkyl such as furfuryl; or R" and R'" combined to form a heterocyclic nitrogen-containing ring such as morpholino, piperidino or a bicyclic ring such as 3-aza (3,2,2)-bicycloheptane; and X is a monovalent anion such as halogen or pseudohalogen, e.g. an anion derived from an inorganic acid such as nitric, nitrous, sulfuric, phosphoric, boric, hydrothiocyanic, cyanic, perchloric, periodic, hydrocyanic, carbonic, hydrofluoric, hydrochloric, hydrobromic, hydroiodic, hydrazoic or hydrogen sulfide; or from an organic acid, e.g. alkanoic acids; i.e., (same or mixed) mono-, di- or tri-bromo, chloro- or fluoro-acetic, n-, or iso-propionic, n-, iso-, or tert.-butyric, etc., acids or substituted carboxylic acid such as (same or mixed) mono-, di- or tri-bromo, chloro- or fluoro-methyl, alkoxy or aryloxy (e.g., 2, 4-dichlorophenoxy) acetic acid, or from an aromatic acid; e.g., benzoic, (same or mixed) or mixed) mono-, di-, or tri-iodo-, bromo- or chlorobenzoic acid, or methoxybenzoic, or nitrobenzoic; or from a carbonic acid monoester such as methyl-, ethyl-, n- and or iso-propyl, n-, iso-, sec- or tert.-butyl, etc., thiocarbonic acid, phenyl thiocarbonic (same or mixed) mono-, di- or tri-chloro-, bromo-, iodo-, lower- alkyl-, or alkoxy-phenyl- carbonic acid or the corresponding di- or tri-thiocarbonic acids. Or mono- or di- (same or mixed) alkyl or aryl mono-, di-, tri- or tetrathio-phosphoric; mono-, di- or tri-thiophosphonic or mono- or dithiophosphinic acids; e.g., O,O-diphenyl phosphorothioic acid, O-alkyl methanephosphonothioic acid, diphenyl phosphinodithioic acid, etc., or alkyl and aryl sulfonic and sulfinic acid; e.g., benzene sulfonic acid, methanesulfinic acid, etc., or in which:

$X^-$ is an anion derived from a mercaptan $R^7SH$ (i.e., has the structure $SR^{-7}$) in which $R^7$ is alkyl, substituted alkyl, aryl, substituted aryl, cycloalkyl, heterocyclic and the like.

Preferred compounds include:

Di-n-butylaminocarbonylmethyl tri-n-butylphosphonium chloride

Diallylaminocarbonylmethyl tri-n-butylphosphonium chloride

Cyclohexylaminocarbonylmethyl tri-n-butylphosphonium chloride 2,4-Dichlorophenylaminocarbonylmethyl tri-n-butylphosphonium chloride N-ethyl N-phenylaminocarbonylmethyl tri-n-butylphosphonium chloride 4-chlorophenylaminocarbonylmethyl tri-n-butylphosphonium chloride Piperidinocarbonylmethyl tri-n-butylphosphonium chloride Furfurylaminocarbonylmethyl tri-n-butylphosphonium chloride Piperidinocarbonylmethyl tri-n-octylphosphonium chloride 4-chlorophenylaminocarbonylmethyl triphenylphosphonium chloride 2,4-Dichlorophenylaminocarbonylmethyl tri-n-butylphosphonium nitrate 2,4-Dichlorophenylaminocarbonylmethyl tri-n-butylphosphonium thiocyanate The types of starting chloroacetamides usable in accordance with the process of present invention are clearly characterized by Formula (II) stated above. These starting compounds are well known and can be prepared readily on an industrial scale.

As examples of such starting, haloacetamides which can be used according to the present invention, there may be mentioned in particular:

2-chloroacetamide
2-chloro-N, N-dimethylacetamide
2-chloro-N, N-diethylacetamide
2-chloro-N-n-butylacetamide 2-chloro-N, N-diallyl acetamide
2-chloro-N-n-octylacetamide
2-chloro-N-n-dodecylacetamide
2-chloro-N-cyclohexylacetamide
2-chloro-N-ethylacetanilide
2-chloro-3'-trifluoromethylacetanilide
2-chloro-4'-chloroacetanilides
2,3',4'-trichloroacetanilide
2,2',4'-trichloroacetanilide
2-chloro-N-ethyl-3',4'-dichloroacetanilide
2-chloro-4'-methylacetanilide
2-chloro-N, N-diethylpropionamide
2-chloroacetylmorpholine
2-chloroacetylpiperidine
2-chloroacetyl-N-methylpiperazine
2-chloroacetyl-N-phenylpiperazine
N-2-chloroacetyl-3-aza-(3,2,2)-bicycloheptane
2-chloro-N-furfurylacetamide
2-bromoacetamide
3-bromo-N, N-diethylpropionamide, and the like.

The types of phosphines usable as starting materials in accordance with the process of the present invention are clearly characterized by Formula (III) stated above.

These starting compounds are also well known and can be readily prepared on an industrial scale. As examples of such starting phosphines which can be used according to the present invention, there may be mentioned in particular:
trimethylphosphine
triethylphosphine
tributylphosphine
tri-n-octylphosphine
tri-n-dodecylphosphine
dimethylphenylphosphine
methyldiphenylphosphine
triallylphosphine
p-chlorophenyldiphenylphosphine
p-chlorophenyldimethylphosphine
hexamethylphosphoroustriamide
diphenyl-p-tolyphosphine
diphenyl-p-chlorophenylphosphine
dibutylmethylphosphine, and the like.

The production reaction is carried out in the presence of an inert solvent (this term also includes a mere diluent). Examples of such solvents are:
benzene, toluene and other aromatic solvents of this type: ethers such as diethyl ether, dimethyl ether or diisopropyl ether;
alcohols such as methanol, ethanol, isopropanol and nitriles such as acetonitrile, propionitrile; ketones such as acetone, methyl ethyl ketone, diethyl ketone or dibutyl ketone; and amides such as dimethylformamide or dimethylacetamide.

The preferred solvents are benzene, ether, acetonitrile and acetone.

Catalysts such as potassium iodide and sodium iodide may be used optionally to facilitate the reaction, if desired.

The reaction temperature may be varied within a fairly wide range. In general, the reaction is carried out at substantially between about 20°–150°C., preferably between 20°–100°C. In general, the reactants are used in approximately equimolar proportions. The order of addition of the reactants can be varied.

After completion of the reaction, evaporation of the volatile constituents is effected in the usual way. The residue may then be recrystallized if a solid or, if an oil, is usually triturated with a non-solvent such as pentane, hexane, heptane, diethyl ether. If the product is still an oil, it is usually subjected to high vacuum for several hours to remove any traces of volatiles.

For the conversion of the various phosphonium chlorides or bromides to the corresponding phosphonium salts of other desired anionic compounds, solvents such as acetone, methanol, ethanol, or water in which both of the reagents are appreciably soluble can be used. After separation of the metal halide (e.g., sodium, potassium, silver or like) formed in the reaction, removal of the solvent under reduced pressure yields the desired salt in substantially pure form.

The compounds according to the present invention exhibit strong growth-regulatory properties and can, therefore, be used to affect the rate of growth of plants. Since at rates and in concentrations showing high growth-regulatory activity the instant active compounds have little or no phytotoxic action, these effects on plant growth can be obtained with little or no damage to useful plants. The instant compounds also possess comparatively low mammalian toxicity.

By plants are meant in the broadest sense all useful vegetation including valuable agricultural, horticultural, fruiticultural, and the like, crop vegetation, weeds, etc., the growth regulation of which is desired.

Thus, the present invention can extend to stunting or retarding the growth of monocotyledonous and dicotyledonous crop and weed plants, ornamental plants, shrubs, and trees; to increasing beneficially the yield, oil yield and protein yield of leguminous plants such as soybeans, lima beans, snap beans, peas, and the like; to affecting the fruit set of spermatophytic plants; i.e., apples, peaches and other fruit of fruit-bearing trees, shrubs or crop plants; to increasing the resistance of vegetation, particularly fruit trees, to the damage caused by frost and drought; to increasing the sugar content or yield of plants such as sugar beet, sugar cane, and the like; to retarding the growth of grasses such as Kentucky Bluegrass, fescue and the like, by reducing both the clipping weight per unit area and the plant height, and thus providing a means of chemical mowing; to inhibiting or partially inhibiting the undesirable growth of suckers on plants, particularly tobacco plants; and to affecting, i.e., breaking, the dormancy of plants, such as potato plants, by causing them to sprout.

As aforesaid, significantly, the instant active compounds can be used in the form of foliar sprays without appreciable phytotoxicity or destruction of chlorphyll; i.e., at the biologiclly efficacious rates normally applied.

The active compounds according to the instant invention can be utilized, if desired, in the form of the usual formulations or compositions with conventional, preferably inert (e.g., plant-compatible or herbicidally inert), pesticide diluents or extenders; i.e., diluents or extenders of the type usable in conventional pesticide-dispersible carrier vehicles such as solutions, emulsions, suspensions, emulsificable concentrates, spray powders, pastes, soluble powders, dusting agents, granules, etc. These are prepared in known manner, for instance by extending the active compound with conventional pesticide-dispersible liquid diluent carriers and/or dispersible solid carriers, optionally with the use of carrier vehicle assistants; e.g., conventional pesticide surface-active agents, including emulsifying agents and/or dispersing agents whereby, for example, in the case where water is used as diluent, organic solvents may be added as auxiliary solvents. The following may be chiefly considered for use as conventional carrier vehicles for the purpose: inert dispersible liquid diluent carriers including inert organic solvents, such as aromatic hydrocarbons (e.g., benzene, toluene, xylene, etc.) halogenated, especially chlorinated, aromatic hydrocarbons (e.g., chlorobenzenes, etc.) paraffins (e.g., petroleum fractions), chlorinated aliphatic hydrocarbons (e.g., dichloromethane, etc.), alcohols (e.g., methanol, ethanol, propanol, butanol, etc.), amines (e.g., 2-aminoethanol, etc.), ethers, etheralcohols (e.g., 2-methoxy ethanol, etc.), amides (e.g., e.g., dimethyl, formamide, etc.), sulfoxides (e.g., dimethyl sulfoxide, etc.), ketones (e.g., acetone, etc.), and/or water; as well as inert, dispersible finely divided solid carriers, such as ground natural minerals (e.g., kaolin, alumina, silica, chalk—calcium carbonate, talc, kieselguhr, etc.), and ground synthetic minerals (e.g., highly dispersed silicic acid, silicates, etc.). Whereas, the following may be chiefly considered for use as conventional carrier vehicle assistants: surface active agents, emulsifying agents, such as non-ionic and/or anionic emulsifying agents (e.g., polyethylene oxide ethers of fatty acids, polyethylene oxide ethers of fatty acids, polyethylene oxide ethers of fatty alcohols, alkyl sulfonates, aryl sulfonates, etc., and especially alkyl arylpolyglycol ethers, magnesium stearate, sodium oleate, etc.), and/or dispersing agents such as lignin, sulfite waste liquors, methyl cellulose, etc.

Such active compounds may be employed alone or in a form of mixtures with one another and/or with such solid and/or liquid dispersible carrier vehicles and/or with other known compatible active agents, especially plant protection agents, such as conventional plant-growth regulators, fungicides, insecticides, nematocides, bactericides, selective herbicides, etc., if desired, or in the form of particular dosage preparations for specific application made therefrom, such as solutions, emulsions, suspensions, powders, pastes, and granules which are thus ready to use.

As concerns comercially marketed preparations, these generally contemplate carrier composition mixtures in which the active compound is present in an amount substantially between about 0.1–95%, and preferably 0.5–90% by weight of the mixture, whereas carrier composition mixtures suitable for direct application or field application generally contemplate those in which the active compound is present in an amount substantially between about 0.01–5%, preferably 0.01–1%, by weight of the mixture. Thus, the present invention contemplates overall compositions which comprise mixtures of a conventional dispersible carrier vehicle such as (1) a dispersible, inert, finely divided carrier solid, and/or (2) a dispersible carrier liquid such as an inert organic solvent and/or water, preferably including a surface-active effective amount of a carrier vehicle assistant; e.g., surface active agent, such as an emulsifying agent and/or a dispersing agent, and an amount of the active compound which is effective for the purpose in question and which is generally between about 0.01–95%, and preferably 0.01–5%, by weight of the mixture.

Conveniently, the instant active compounds, having appreciable solubility in water, are preferably usable in the form of aqueous solutions containing substantially between 0.01 and 5%, preferably 0.01–1%, by weight of the active compound, with or without the addition of stabilizers, surface active agents, etc., as mentioned above. Such solutions are particularly useful for direct foliar spray application, without causing appreciable phytotoxic plant injury at efficacious growth-regulating rates of application.

The active compounds can also be used in accordance with the well-known ultra-low-volume process with good success; i.e., by applying such compound if normally a liquid, or by applying a liquid composition containing the same, via very effective atomizing equipment, in finely divided form; e.g., average particle diameter of from 50–100 microns, or even less (mist form) for example by airplane-crop-spraying techniques. Only up to at most about a few liters/hectare are needed, and often amounts only up to 1 quart/acre, preferably 2–16 fluid ounces/acre, are sufficient. In this process it is possible to use highly concentrated liquid compositions with said liquid carrier vehicles containing from about 20 to about 95% by weight of the active compound or even the 100% active substance alone.

Furthermore, the present invention contemplates methods of selectively controlling the rate of growth of plants; e.g., stunting plant growth, increasing plant or fruit yield, protein yield, oil yield, sugar yield, resistance to frost and drought damage, synergizing defoliating action and inhibiting regrowth, effecting chemical mowing, preventing the growth of undesirable suckers, breaking plant dormancy and the like, which comprise applying to at least one of (a) such plants and (b) their habitat (the locus to be protected or controlled) an efficacious or growth-rate-controlling amount of the particular active compound of the invention alone or together with a carrier vehicle as noted above. The instant formulations or compositions are applied in the usual manner, for example, by spraying, atomizing, scattering, dusting, watering, sprinkling and the like, either to the soil around the plants, the plants themselves, or both.

It will be realized, of course, that in connection with use of the instant compounds for influencing the growth of plants and/or effecting the other desirable results heretofore mentioned, the concentration of the particular active compound utilized in admixture with the carrier vehicle will depend upon the intended application and may be varied within a fairly wide range depending upon the weather conditions, the purpose for which the active compound is used (e.g., growth-promoting or growth-retarding effect) and the plant species in which it is intended to produce the desired effect. Therefore, in special cases, it is possible to go above or below the aforementioned concentration ranges.

The outstanding growth-regulatory activity of the particular active compounds of the present invention is illustrated, without limitation, by the following examples.

EXAMPLE 1

Cucumber Root Growth Test
Wettable powder base consisting of:
92 parts by weight hydrated silica (ultra fine, "Hi-Sil 233")
4 parts by weight sodium lignin sulfonate (Marasperse N")
4 parts by weight polycondensate of ethylene oxide, propylene oxide and propylene glycol (mol. wt. about 1,000) ("Pluronic L-71")

To produce a suitable preparation of the particular active compound, 1 part by weight of such active compound is mixed intimately with 1 part by weight of the stated wettable powder base, and the resulting mixture is diluted with water to the desired final concentration. A piece of round filter paper (150 mm. diameter) is placed in a 150 mm × 25 mm Petri dish, and 10 cucumber seeds are arranged in a row on the paper. The filter paper is then moistened with 7 ml of the preparation of the given active compound.

The so-treated dish is incubated in darkness at 22°C. Rating is determined on the basis of growth response of the root during the period of 24 hours between the third and fourth day of incubation.

A 0 to 9 scale rating is used to indicated the activity of potential growth retardants. A 0 scale reading indicates growth retardation within the range of 0–10% as compared with the control. A 9 scale reading cooresponds to 90% or more growth retardation. On the other hand, figures in parentheses indicate growth promotion or enhancement. Thus, a (0) to (9) scale rating is used to indicate the activity of potential growth promotants. (0) indicates growth promotion within the range of 0–10% as compared with the control, whereas (9) indicates 90% or greater growth promotion when compared with the control.

The particular active compounds tested the amounts used and the results obtained can be seen from the following Table 1.

Table 1

| Active Compound | Concentration (ppm.) | | |
|---|---|---|---|
| | 10,000 | 1,000 | 100 |
| $(n\text{-}C_4H_9)_3 \overset{+}{P}\text{—}CH_2\text{—}\overset{O}{\underset{\|}{C}}\text{—}NH_2 \cdot Cl^-$ | 9 | 3 | 3 |
| $(n\text{-}C_4H_9)_3 \overset{+}{P}\text{—}CH_2\text{—}\overset{O}{\underset{\|}{C}}\text{—}N(CH_3)_2 \cdot Cl^-$ | 9 | 9 | 6 |
| $(n\text{-}C_4H_9)_3 \overset{+}{P}\text{—}CH_2\text{—}\overset{O}{\underset{\|}{C}}\text{—}N(C_2H_5)_2 \cdot Cl^-$ | 9 | 9 | 6 |
| $(n\text{-}C_4H_9)_3 \overset{+}{P}\text{—}CH_2\text{—}\overset{O}{\underset{\|}{C}}\text{—}N(n\text{-}C_4H_9)_2 \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}NH(n\text{-}C_8H_{17}) \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}N(CH_2\text{—}CH{=}CH_2)_2 \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}NH\text{—}\langle S \rangle \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}\underset{CH_3}{N}\text{—}CH_2\text{—}\langle C_6H_4 \rangle\text{—}Cl \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}NH\,CH_2\text{—}\langle C_6H_3(Cl) \rangle\text{—}Cl \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}\underset{C_2H_5}{N}\text{—}C_6H_5 \cdot Cl^-$ | 9 | 9 | 8 |
| $(n\text{-}C_4H_9)_3 \overset{+}{P}\text{—}CH_2\overset{O}{\underset{\|}{C}}\text{—}\underset{CH_3}{N}\text{—}\langle C_6H_3(CH_3) \rangle \cdot Cl^-$ | 9 | 9 | (2) |
| $(n\text{-}C_4H_9)_3 \overset{+}{P}\text{—}CH_2\text{—}\overset{O}{\underset{\|}{C}}\text{—}NH\text{—}\langle C_6H_3(CH_3)_2 \rangle \cdot Cl^-$ | 9 | 9 | 7 |
| $(n\text{-}C_4H_9)_3 \overset{+}{P}CH_2\text{—}\overset{O}{\underset{\|}{C}}\text{—}NH\text{—}\langle C_6H_4 \rangle\text{—}Cl \cdot Cl^-$ | 9 | 9 | 9 |
| $(n\text{-}C_4H_9)_3 \overset{+}{P}\text{—}CH_2\text{—}\overset{O}{\underset{\|}{C}}\text{—}NH\text{—}\langle C_6H_3(Cl) \rangle\text{—}Cl \cdot Cl^-$ | 9 | 9 | 9 |

Table 1-continued

| Active Compound | Concentration (ppm.) | | |
|---|---|---|---|
| | 10,000 | 1,000 | 100 |
| $(n-C_4H_9)_3 \overset{+}{P}-\underset{\underset{CH_3}{|}}{CH}-\overset{O}{\overset{\|}{C}}-NH-\underset{Cl}{\overset{Cl}{\bigcirc}} \cdot Cl^-$ | 9 | 8 | 1 |
| $(n-C_4H_9)_3 \overset{+}{P}-CH_2-\overset{O}{\overset{\|}{C}}-\underset{\underset{CH_3}{|}}{N}-\underset{}{\overset{CF_3}{\bigcirc}} \cdot Cl^-$ | 9 | 9 | (2) |
| $(n-C_4H_9)_3 \overset{+}{P}-CH_2-\overset{O}{\overset{\|}{C}}-\underset{\underset{C_2H_4CN}{|}}{N}-\bigcirc \cdot Cl^-$ | 9 | 8 | 4 |
| $(n-C_4H_9)_3 \overset{+}{P}-CH_2-\overset{O}{\overset{\|}{C}}-N\diagup\diagdown O \cdot Cl^-$ | 9 | 6 | (1) |
| $(n-C_4H_9)_3 \overset{+}{P}-CH_2-\overset{O}{\overset{\|}{C}}-N\diagup\diagdown \cdot Cl^-$ | 9 | 9 | 9 |
| $(n-C_4H_9)_3 \overset{+}{P}-CH_2-\overset{O}{\overset{\|}{C}}-NH\ CH_2-\underset{O}{\diagdown\diagup} \cdot Cl^-$ | 9 | 9 | 8 |
| $[(CH_3)_2N]_3 \overset{+}{P}-CH_2-\overset{O}{\overset{\|}{C}}-NH_2 \cdot Cl^-$ | 9 | 8 | 2 |
| $[(CH_3)_2N]_3 \overset{+}{P}-CH_2-\overset{O}{\overset{\|}{C}}-N(C_2H_5)_2 \cdot Cl^-$ | 7 | 1 | 0 |
| $[(CH_3)_2N]_3 \overset{+}{P}-CH_2-\overset{O}{\overset{\|}{C}}-\underset{\underset{C_6H_5}{|}}{N}-C_2H_5 \cdot Cl^-$ | 9 | 9 | 5 |
| $[(CH_3)_2N]_3 \overset{+}{P}-CH_2-\overset{O}{\overset{\|}{C}}-NH\diagup S \cdot Cl^-$ | 8 | 4 | 0 |
| $(n-C_8H_{17})_3 \overset{+}{P}-CH_2-\overset{O}{\overset{\|}{C}}-N(C_2H_5)_2 \cdot Cl^-$ | 9 | 9 | 6 |
| $(n-C_8H_{17})_3 \overset{+}{P}-CH_2-\overset{O}{\overset{\|}{C}}-NH(n-C_8H_{17}) \cdot Cl^-$ | 6 | 6 | 5 |
| $(n-C_8H_{17})_3 \overset{+}{P}-CH_2-\overset{O}{\overset{\|}{C}}-N(CH_2CH=CH_2)_2 \cdot Cl^-$ | 9 | 8 | 2 |
| $(n-C_8H_{17})_3 \overset{+}{P}-CH_2-\overset{O}{\overset{\|}{C}}-N\diagup\diagdown O \cdot Cl^-$ | 9 | 9 | 5 |
| $(n-C_8H_{17})_3 \overset{+}{P}-CH_2-\overset{O}{\overset{\|}{C}}-N\diagup\diagdown \cdot Cl^-$ | 9 | 9 | 9 |
| $(n-C_8H_{17})_3 \overset{+}{P}-CH_2-\overset{O}{\overset{\|}{C}}-NH-\underset{CH_3}{\overset{CH_3}{\bigcirc}} \cdot Cl^-$ | 9 | (1) | (1) |
| $(n-C_8H_{17})_3 \overset{+}{P}-CH_2-\overset{O}{\overset{\|}{C}}-NH-\bigcirc-Cl \cdot Cl^-$ | 6 | 5 | 0 |
| $(C_6H_5)_3 \overset{+}{P}-CH_2-\overset{O}{\overset{\|}{C}}-N(C_2H_5)_2 \cdot Cl^-$ | 9 | 8 | 4 |
| $(C_6H_5)_3 \overset{+}{P}-CH_2-\overset{O}{\overset{\|}{C}}-N(CH_2CH=CH_2)_2 \cdot Cl^-$ | 9 | 9 | 7 |

Table 1-continued

| Active Compound | Concentration (ppm.) | | |
|---|---|---|---|
| | 10,000 | 1,000 | 100 |
| $(C_6H_5)_3\overset{+}{P}-CH_2-\overset{O}{\underset{\|}{C}}-NH-\underset{}{\langle\bigcirc\rangle}-Cl \cdot Cl^-$ | 9 | 9 | 9 |
| $(C_6H_5)_3\overset{+}{P}-CH_2-\overset{O}{\underset{\|}{C}}-NH-\underset{CH_3}{\overset{CH_3}{\langle\bigcirc\rangle}}-Cl^-$ | 9 | 9 | 9 |
| $(C_6H_5)_3\overset{+}{P}-CH_2-\overset{O}{\underset{\|}{C}}-N\langle\bigcirc\rangle \cdot Cl^-$ (piperidine) | 9 | 8 | 2 |
| $(C_6H_5)_3\overset{+}{P}-CH_2-\overset{O}{\underset{\|}{C}}-N\langle\bigcirc\rangle O \cdot Cl^-$ (morpholine) | 9 | 7 | 1 |
| $(C_6H_5)_2(p\text{-}CH_3C_6H_4)\overset{+}{P}-CH_2-\overset{O}{\underset{\|}{C}}-N(C_2H_5)_2 \cdot Cl^-$ | 9 | 9 | 7 |
| $(C_6H_5)_2(p\text{-}CH_3C_6H_4)\overset{+}{P}-CH_2-\overset{O}{\underset{\|}{C}}-NH-\langle\bigcirc\rangle-Cl \cdot Cl^-$ | 9 | 9 | 8 |
| $(C_6H_5)_2(p\text{-}CH_3C_6H_4)\overset{+}{P}-CH_2-\overset{O}{\underset{\|}{C}}-NH-\underset{CH_3}{\overset{CH_3}{\langle\bigcirc\rangle}} \cdot Cl^-$ | 9 | 9 | 6 |
| $(C_6H_5)_2(p\text{-}CH_3C_6H_4)\overset{+}{P}-CH_2-\overset{O}{\underset{\|}{C}}-N\langle\bigcirc\rangle \cdot Cl^-$ | 9 | 9 | 9 |
| $(CH_3)_2(C_6H_5)\overset{+}{P}-CH_2-\overset{O}{\underset{\|}{C}}-NH-\langle\bigcirc\rangle \cdot Cl^-$ | 9 | 9 | 6 |
| $(CH_3)_2(C_6H_5)\overset{+}{P}-CH_2-\overset{O}{\underset{\|}{C}}-N(C_2H_5)_2 \cdot Cl^-$ | 8 | 8 | 4 |
| $(n\text{-}C_4H_9)_3\overset{+}{P}-CH_2-\overset{O}{\underset{\|}{C}}-NH_2 \cdot NO_3^-$ | 9 | 9 | 3 |
| $(n\text{-}C_4H_9)_3\overset{+}{P}-CH_2-\overset{O}{\underset{\|}{C}}-N(C_2H_5)_2 \cdot NO_3^-$ | 9 | 9 | 7 |
| $(n\text{-}C_8H_{17})_3\overset{+}{P}-CH_2-\overset{O}{\underset{\|}{C}}-N(C_2H_5)_2 \cdot NO_3^-$ | 9 | 9 | 6 |
| $[(CH_3)_2N]_3\overset{+}{P}-CH_2-\overset{O}{\underset{\|}{C}}-\underset{\overset{\|}{C_2H_5}}{N}-\langle\bigcirc\rangle \cdot NO_3^-$ | 9 | 8 | 3 |
| $(n\text{-}C_4H_9)_3\overset{+}{P}-\underset{\overset{\|}{CH_3}}{CH}-\overset{O}{\underset{\|}{C}}-NH-\underset{Cl}{\overset{Cl}{\langle\bigcirc\rangle}} \cdot NO_3^-$ | 9 | 9 | 9 |
| $(n\text{-}C_4H_9)_3\overset{+}{P}-CH_2-\overset{O}{\underset{\|}{C}}-NH-\underset{}{\overset{Cl}{\langle\bigcirc\rangle}}-Cl \cdot NO_3^-$ | 9 | 9 | 9 |
| $(n\text{-}C_4H_9)_3\overset{+}{P}-CH_2-\overset{O}{\underset{\|}{C}}-NH-CH_2-\langle\text{furan}\rangle \cdot NO_3^-$ | 9 | 9 | 7 |
| $(C_4H_9)_3\overset{+}{P}-CH_2-\overset{O}{\underset{\|}{C}}-N(C_2H_5)_2 \cdot I^-$ | 9 | 9 | 8 |
| $(n\text{-}C_4H_9)_3\overset{+}{P}-CH_2-\overset{O}{\underset{\|}{C}}-NH_2 \cdot SCN^-$ | 9 | 9 | 4 |

Table 1-continued

| Active Compound | Concentration (ppm.) 10,000 | 1,000 | 100 |
|---|---|---|---|
| $(C_4H_9)_3 \overset{+}{P}-CH_2-\overset{O}{\underset{\|\|}{C}}-N(C_2H_5)_2 \cdot SCN^-$ | 9 | 9 | 9 |
| $(n\text{-}C_4H_9)_3 \overset{+}{P}-CH_2-\overset{O}{\underset{\|\|}{C}}-NH-\phenyl\text{-}S \cdot SCN^-$ | 9 | 9 | 8 |
| $(n\text{-}C_4H_9)_3 \overset{+}{P}-CH_2-\overset{O}{\underset{\|\|}{C}}-NH-\text{(Cl)phenyl}-Cl \cdot SCN^-$ | 9 | 9 | 9 |
| $(n\text{-}C_4H_9)_3 \overset{+}{P}-CH_2-\overset{O}{\underset{\|\|}{C}}-NH-CH_2-\text{furyl} \cdot SCN^-$ | 9 | 9 | 8 |
| $(n\text{-}C_4H_9)_3 \overset{+}{P}-CH_2-\overset{O}{\underset{\|\|}{C}}-NH_2 \cdot {}^-O\overset{O}{\underset{\|\|}{C}}-CH_3$ | 9 | 8 | 3 |
| $(C_4H_9)_3 \overset{+}{P}-CH_2-\overset{O}{\underset{\|\|}{C}}-N(C_2H_5)_2 \cdot O\overset{O}{\underset{\|\|}{C}}-CH_3$ | 9 | 9 | 7 |
| $(n\text{-}C_4H_9)_3 \overset{+}{P}-CH_2-\overset{O}{\underset{\|\|}{C}}-NH_2 \cdot {}^-S\overset{S}{\underset{\|\|}{C}}N(CH_3)_2$ | 9 | 9 | 5 |
| $(C_4H_9)_3 \overset{+}{P}-CH_2-\overset{O}{\underset{\|\|}{C}}-N(C_2H_5)_2 \cdot \overset{S}{\underset{\|\|}{SCN(CH_3)_2}}$ | 9 | 9 | 8 |
| $[(CH_3)_2N]_3 \overset{+}{P}-CH_2-\overset{O}{\underset{\|\|}{C}}-\underset{C_2H_5}{\overset{\|}{N}}-\text{phenyl} \cdot \overset{S}{\underset{\|\|}{SCN(CH_3)_2}}$ | 9 | 8 | 1 |
| $(n\text{-}C_4H_9)_3 \overset{+}{P}-\underset{CH_3}{\overset{\|}{CH}} C NH-\text{(Cl)phenyl}-Cl \cdot \overset{S}{\underset{\|\|}{SCN(CH_3)_2}}$ (with C=O) | 9 | 9 | 9 |
| $(C_4H_9)_3 \overset{+}{P}-CH_2-\overset{O}{\underset{\|\|}{C}}-N(C_2H_5)_2 \cdot \overset{S}{\underset{\|\|}{SCO}} C_2H_5$ | 9 | 9 | 7 |
| $(n\text{-}C_4H_9)_3 \overset{+}{P}-CH_2-\overset{O}{\underset{\|\|}{C}}-NH-\text{phenyl} \cdot \overset{O}{\underset{\|\|}{OS}}C_6H_5$ | 9 | 9 | 9 |

The following further examples are set forth to illustrate, without limitation, the process for producing the active compounds according to the present invention.

EXAMPLE 2

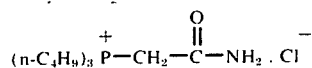

To a solution of 9.4 g (0.1 mole) of 2 chloroacetamide, dissolved in 300 ml of acetone, was added 20.3 g (0.1 mole) of tri-n-butylphosphine. The reaction mixture was allowed to stand at room temperature for 4 days after which the solvent was removed by distillation under vacuum leaving a semi-solid residue. This was triturated with ether to give 29.2 g (98%) of a white solid, m.p. 143°–145°C.
Analysis: Calc. for nitrogen, 4.73%; found, 4.92%

EXAMPLE 3

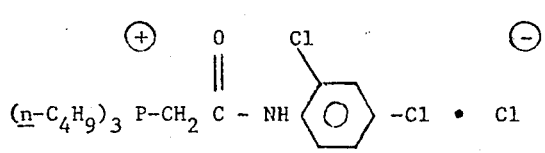

To a solution of 35.7 g (0.15 mole) 2, 2', 4' trichloroacetanilide dissolved in 600 ml of methanol was added 30.3 g (0.15 mole) of tri-n-butylphosphine. The reaction mixture was refluxed for 48 hours, and the solvent removed by distillation under reduced pressure. The residue was triturated with ether, and the residual oil was 39.8 g (60%).
Analysis:

calc. for nitrogen 3.17%; found, 2.88%.
calc. for phosphorus 7.03%; found, 6.00%.
calc. for ionic chlorine 8.05%; found 7.38%.

EXAMPLE 4

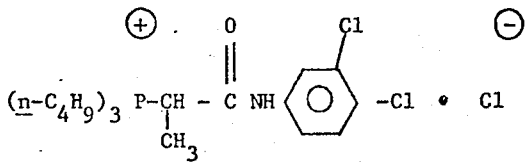

To a mixture of 25.3 gms. (0.1 mole) of 2, 3', 4', trichloropropionanilide in 500 ml of acetonitrile was added 20.2 g, (0.1 mole) of tri-n-butylphosphine. The reaction mixture was refluxed for 6 days, and the solvents were removed by distillation under reduced pressure. The residual oil was triturated with ether followed with ethyl acetate, and again the solvents were removed by distillation under reduced pressure. The oil was subjected to a vacuum of 0.1 mm for 1 hour. The product thus obtained was a pale yellow syrup weighing 37 g (81%).

Analysis:
  calc. for nitrogen 3.08; found, 2.87.
  calc. for ionic chlorine 7.8%; found 7.3.

The following compounds are prepared in analogous manner:

| Active Compound | |
|---|---|
| $(n\text{-}C_4H_9)_3 \overset{+}{P}\text{—}CH_2\text{—}\overset{O}{\underset{\|}{C}}\text{—}N(CH_3)_2 \cdot Cl^-$ | colorless viscous oil |
| $(n\text{-}C_4H_9)_3 \overset{+}{P}\text{—}CH_2\text{—}\overset{O}{\underset{\|}{C}}\text{—}N(C_2H_5)_2 \cdot Cl^-$ | colorless viscous oil |
| $(n\text{-}C_4H_9)_3 \overset{+}{P}\text{—}CH_2\text{—}\overset{O}{\underset{\|}{C}}\text{—}N(C_4H_9\text{-}n)_2 \cdot Cl^-$ | yellow viscous oil |
| $(n\text{-}C_4H_9)_3 \overset{+}{P}\text{—}CH_2\overset{O}{\underset{\|}{C}}\text{—}NH(n\text{-}C_8H_{17}) \cdot Cl^-$ | amber viscous oil |
| $(n\text{-}C_4H_9)_3 \overset{+}{P}\text{—}CH_2\text{—}\overset{O}{\underset{\|}{C}}\text{—}N(CH_2\text{—}CH=CH_2)_2 \cdot Cl^-$ | amber viscous oil |
| $(n\text{-}C_4H_9)_3 \overset{+}{P}\text{—}CH_2\text{—}\overset{O}{\underset{\|}{C}}\text{—}NH\text{—}\langle S \rangle \cdot Cl^-$ | tan semi-solid |
| $(n\text{-}C_4H_9)_3 \overset{+}{P}\text{—}CH_2\text{—}\overset{O}{\underset{\|}{C}}\text{—}\underset{CH_3}{N}\text{—}CH_2\text{—}\langle C_6H_4\text{-}Cl \rangle \cdot Cl^-$ | yellow viscous oil |
| $(n\text{-}C_4H_9)_3 \overset{+}{P}\text{—}CH_2\text{—}\overset{O}{\underset{\|}{C}}\text{—}NH(CH_2\text{—}\langle 2\text{-}Cl\text{-}C_6H_4 \rangle) \cdot Cl^-$ | amber viscous oil |
| $(n\text{-}C_4H_9)_3 \overset{+}{P}\text{—}CH_2\overset{O}{\underset{\|}{C}}\text{—}\underset{C_2H_5}{N}\text{—}C_6H_5 \cdot Cl^-$ | Hygroscopic white waxy solid |
| $(n\text{-}C_4H_9)_3 \overset{+}{P}\text{—}CH_2\text{—}\overset{O}{\underset{\|}{C}}\text{—}\underset{CH_3}{N}\text{—}\langle 2\text{-}CH_3\text{-}C_6H_4 \rangle \cdot Cl^-$ | viscous amber oil |
| $(n\text{-}C_4H_9)_3 \overset{+}{P}\text{—}CH_2\text{—}\overset{O}{\underset{\|}{C}}\text{—}NH\langle 2,6\text{-}(CH_3)_2\text{-}C_6H_3 \rangle \cdot Cl^-$ | m.p. 118–21°C |
| $(n\text{-}C_4H_9)_3 \overset{+}{P}\text{—}CH_2\text{—}\overset{O}{\underset{\|}{C}}\text{—}NH\text{—}\langle 4\text{-}Cl\text{-}C_6H_4 \rangle \cdot Cl^-$ | m.p. 159–161°C |
| $(n\text{-}C_4H_9)_3 \overset{+}{P}\text{—}CH_2\text{—}\overset{O}{\underset{\|}{C}}\text{—}NH\text{—}\langle 3,4\text{-}Cl_2\text{-}C_6H_3 \rangle \cdot Cl^-$ | m.p. 138–42°C |
| $(n\text{-}C_4H_9)_3 \overset{+}{P}\text{—}\underset{CH_3}{CH}\text{—}\overset{O}{\underset{\|}{C}}\text{—}NH\text{—}\langle 3,4\text{-}Cl_2\text{-}C_6H_3 \rangle \cdot Cl^-$ | viscous amber oil |
| $(n\text{-}C_4H_9)_3 \overset{+}{P}\text{—}CH_2\text{—}\overset{O}{\underset{\|}{C}}\text{—}\underset{CH_3}{N}\text{—}\langle 2\text{-}CF_3\text{-}C_6H_4 \rangle \cdot Cl^-$ | viscous amber oil |

-continued
| Active Compound | |
|---|---|
| 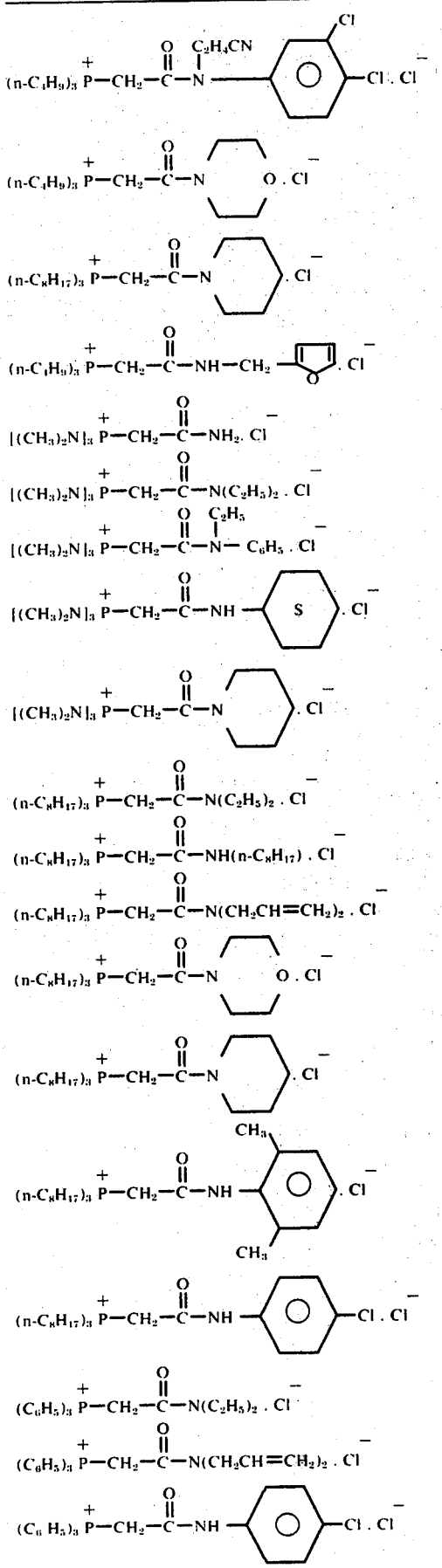 | yellow viscous liquid |
| | amber oil |
| | viscous amber oil |
| | black semi-solid |
| | amber glass |
| | amber viscous oil |
| | tan waxy solid |
| | m.p. 213–15°C |
| | amber viscous oil |
| | amber viscous oil |
| | amber viscous oil |
| | yellow viscous oil |
| | yellow viscous oil |
| | yellow viscous oil |
| | m.p. 65–66°C |
| | m.p. 200–204°C |
| | m.p. 166–69°C |
| | m.p. 270°C (dec.) |

| Active Compound | |
|---|---|
| (C₆H₅)₃ P⁺—CH₂—C(=O)—NH—(2,6-dimethylphenyl) . Cl⁻ | m.p. 180–2°C |
| (C₆H₅)₃ P⁺—CH₂—C(=O)—N(piperidinyl) . Cl⁻ | m.p. 167–8°C |
| (C₆H₅)₃ P⁺—CH₂—C(=O)—N(morpholinyl) . Cl⁻ | m.p. 205–8°C |
| (C₆H₅)₂(p-CH₃C₆H₄) P⁺—CH₂—C(=O)—N(C₂H₅)₂ . Cl⁻ | hygroscopic solid |
| (C₆H₅)₂(p-CH₃C₆H₄) P⁺—CH₂—C(=O)—NH—(C₆H₄-Cl) . Cl⁻ | m.p. 147–9°C |
| (C₆H₅)₂(p-CH₃C₆H₄) P⁺—CH₂—C(=O)—NH—(2,6-dimethylphenyl) . Cl⁻ | m.p. 248–52°C |
| (C₆H₅)₂(p-CH₃C₆H₄) P⁺—CH₂—C(=O)—N(piperidinyl) . Cl⁻ | m.p. 108–110°C |
| (CH₃)₂(C₆H₅) P⁺—CH₂—C(=O)—NH—(C₆H₄-Cl) . Cl⁻ | m.p. 226–30°C |
| (CH₃)₂(C₆H₅) P⁺—CH₂—C(=O)—N(C₂H₅)₂ . Cl⁻ | m.p. 215–17°C |

EXAMPLE 5

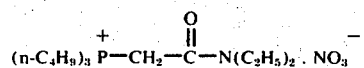

(n-C₄H₉)₃ P⁺—CH₂—C(=O)—N(C₂H₅)₂ . NO₃⁻

To a solution of 3.1 g (0.018 mole) of silver nitrate in 200 ml of boiling ethanol were added 6.5 g (0.018 mole) of diethylaminocarbonylmethyl tri-n-butyl phosphonium chloride in 50 ml of ethanol. The reaction mixture was stirred vigorously for one hour and allowed to come to room temperature. The suspension was filtered and the volatile solvents were removed by distillation under reduced pressure. The residue was dissolved in acetone and filtered again and the volatile solvents were again removed in the usual manner. The yield of product was 6 g (88%) of a black viscous oil.

Analysis:
  calc for nitrogen 7.4%; found 7.137.
  calc. for phosphorus 8.2%; found 7.87.

The following compounds are prepared in an analogous manner, using silver nitrate for the nitrates and using the corresponding sodium, potassium or ammonium salts for the other anions:

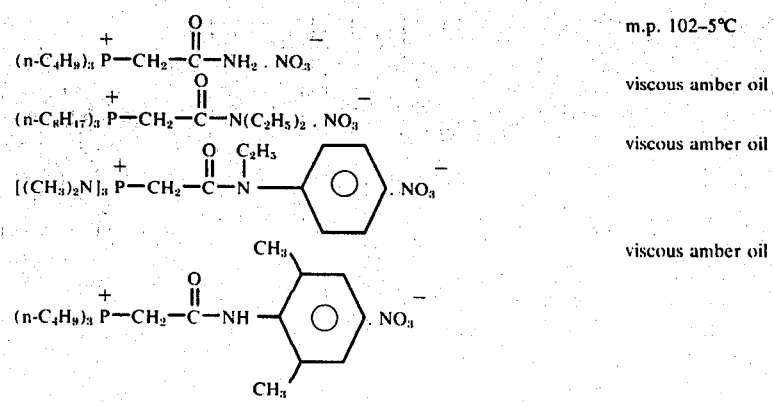

| | |
|---|---|
| (n-C₄H₉)₃ P⁺—CH₂—C(=O)—NH₂ . NO₃⁻ | m.p. 102–5°C |
| (n-C₈H₁₇)₃ P⁺—CH₂—C(=O)—N(C₂H₅)₂ . NO₃⁻ | viscous amber oil |
| [(CH₃)₂N]₃ P⁺—CH₂—C(=O)—N(C₂H₅)(C₆H₅) . NO₃⁻ | viscous amber oil |
| (n-C₄H₉)₃ P⁺—CH₂—C(=O)—NH—(2,6-dimethylphenyl) . NO₃⁻ | viscous amber oil |

-continued

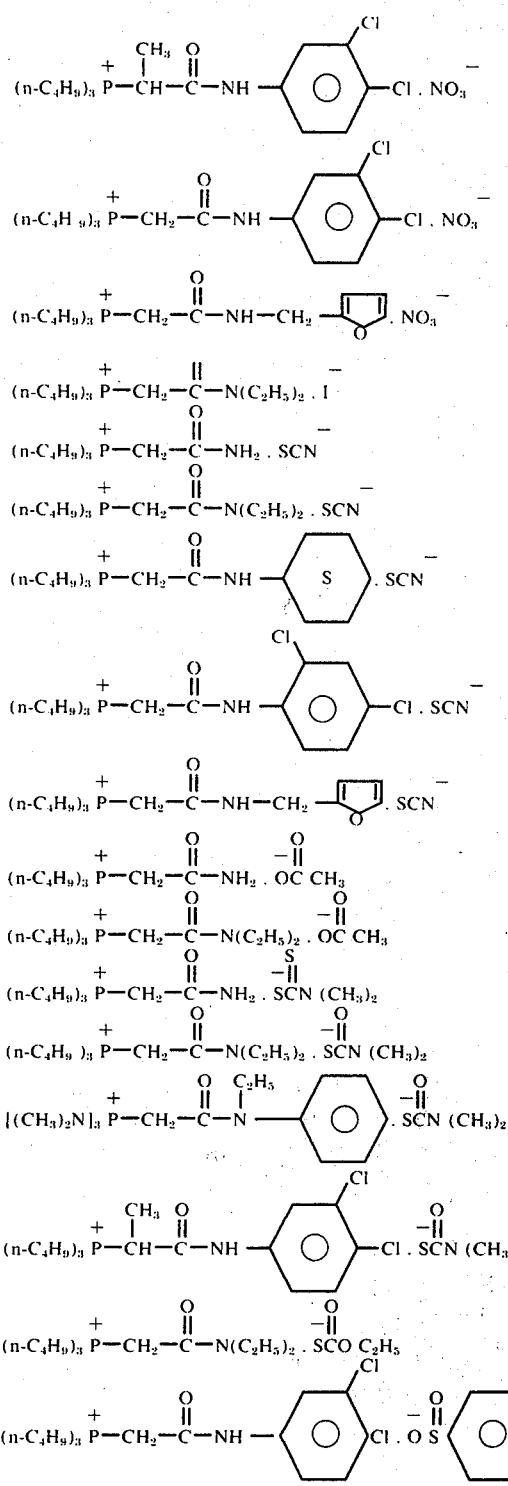

| | |
|---|---|
| | viscous amber oil |
| | viscous amber oil |
| | viscous amber oil |
| | dark red oil |
| | m.p. 61–3°C |
| | red viscous oil |
| | brown semi-solid |
| | viscous amber oil |
| | viscous amber oil |
| | m.p. 103–5°C |
| | viscous amber oil |
| | m.p. 146–8°C |
| | viscous amber oil |
| | viscous amber oil |
| | m.p. 130–3°C |
| | viscous amber oil |
| | m.p. 79–81°C |

It will be realized by the artisan that all of the foregoing compounds contemplated by the present invention possess one or more of the desired plant-growth-regulating properties, as well as a comparatively low phytotoxicity and a concomitantly low mammalian toxicity, enabling such compounds to be used with correspondingly favorable compatibility with warm-blooded creatures for more effective growth-regulating; e.g., growth-promoting and growth-retarding, purposes.

It will be appreciated that the instant specification and examples are set forth by way of illustration and not limitation, and that various modifications and changes may be made without departing from the spirit and scope of the present invention, which is to be limited only by the scope of the appended claims.

What is claimed is:

1. Quaternary phosphonium carboxamide salts of the formula

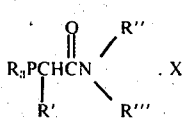 (I)

wherein
R is alkyl of 1–14 carbons or dimethylamino,
R' is hydrogen or lower alkyl;
R" and R''' each is hydrogen, alkyl of 1–14 carbon atoms, cycloalkyl of 3–7 carbon atoms, alkenyl of 2–6 carbon atoms, aralkyl having 1–4 carbon atoms in each corresponding alkyl moiety and optionally substituted with 1–3 chlorine atoms, phenyl, phenyl substituted with 1–3 chloro or 1–2 alkyl groups having 1–3 carbon atoms; and
$X^-$ is a monovalent anion.

2. A salt according to claim 1, wherein
R is alkyl of up to 8 carbon atoms,
R' is hydrogen, and
X is a chloride, nitrate or thiocyanate anion.

3. A salt according to claim 2, wherein R is butyl.

4. A salt according to claim 3 wherein the salt is di-n-butylaminocarbonylmethyl tri-n-butylphosphonium chloride of the formula

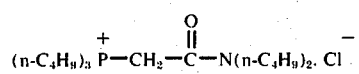

5. A salt according to claim 3 wherein the salt is diallylaminocarbonylmethyl tri-n-butylphosphonium chloride of the formula

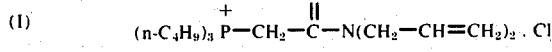

6. A salt according to claim 3 wherein the salt is cyclohexylaminocarbonylmethyl tri-n-butylphosphonium chloride of the formula

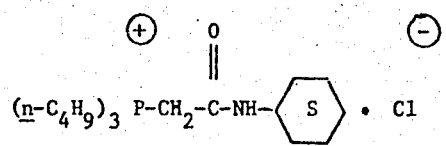

7. A salt according to claim 3 wherein the salt is 2,4-dichlorophenylaminocarbonylmethyl tri-n-butylphosphonium chloride of the formula

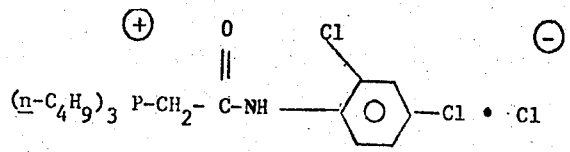

8. A salt according to claim 3 wherein the salt is N-ethyl N-phenylaminocarbonylmethyl tri-n-butylphosphonium chloride of the formula

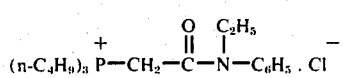

9. A salt according to claim 1, wherein
R is alkyl of 1–14 carbon atoms, and
R" is hydrogen, alkyl of 1–14 carbon atoms or alkenyl of 2–6 carbon atoms.

* * * * *